US00PP32414P2

(12) United States Plant Patent
Hughes

(10) Patent No.: US PP32,414 P2
(45) Date of Patent: Oct. 27, 2020

(54) ***SEDUM* PLANT NAMED 'GOLD FORM'**

(50) Latin Name: *Sedum rupestre*
Varietal Denomination: Gold Form

(71) Applicant: Jared Edward Hughes, Marengo, OH (US)

(72) Inventor: Jared Edward Hughes, Marengo, OH (US)

( * ) Notice: Subject to any disclaimer, the term of this patent is extended or adjusted under 35 U.S.C. 154(b) by 0 days.

(21) Appl. No.: 16/602,290

(22) Filed: Sep. 6, 2019

(51) Int. Cl.
*A01H 5/02* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
CPC ..... A01H 5/02; A01H 5/00
See application file for complete search history.

(56) References Cited

PUBLICATIONS https://garden.org/plants/view/784453/Jennys-Stonecrop-Petrosedum-rupestre-subsp-rupestre-Prima-Angelina/; Feb. 25, 2020; 4 pages.*
https://www.floraldaily.com/article/9090946/what-was-on-display-at-ball-horticultural-during-cast/; Apr. 10, 2019; 15 pages.*

* cited by examiner

*Primary Examiner* — Kent L Bell
(74) *Attorney, Agent, or Firm* — C. A. Whealy

(57) ABSTRACT

A new and distinct cultivar of *Sedum* plant named 'Gold Form', characterized by its compact, dense and bushy growth habit; initially upright to trailing to weeping and decumbent plant habit; freely basally and laterally branching habit; yellow green-colored leaves; and good garden performance and winter hardiness.

2 Drawing Sheets

Figure 1:
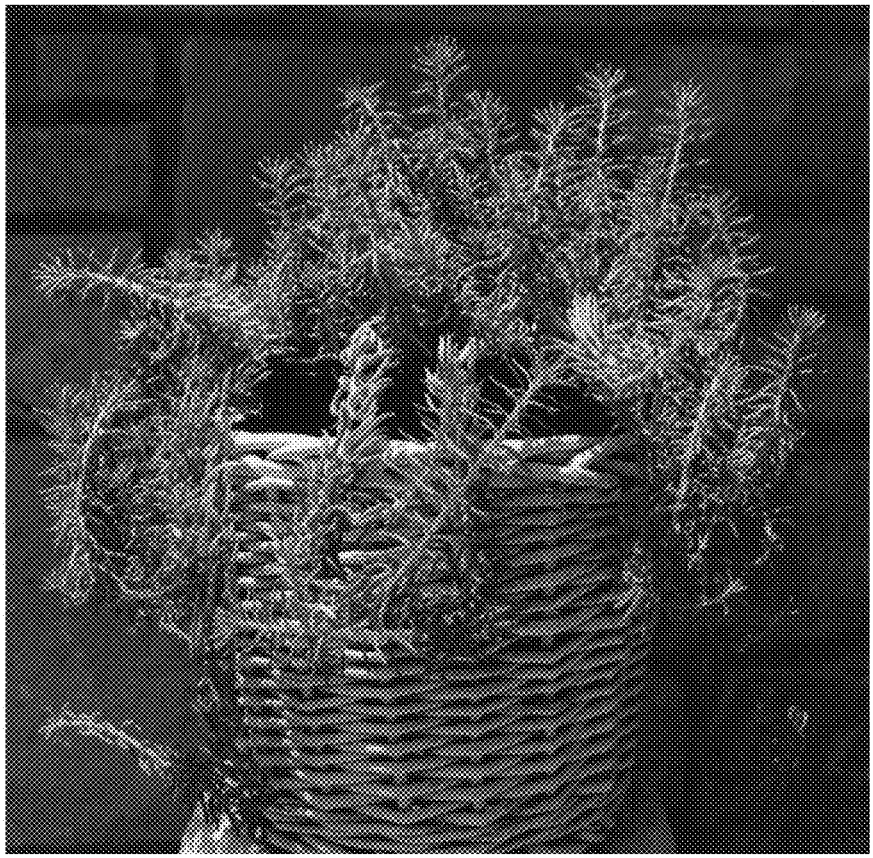
Figure 2:
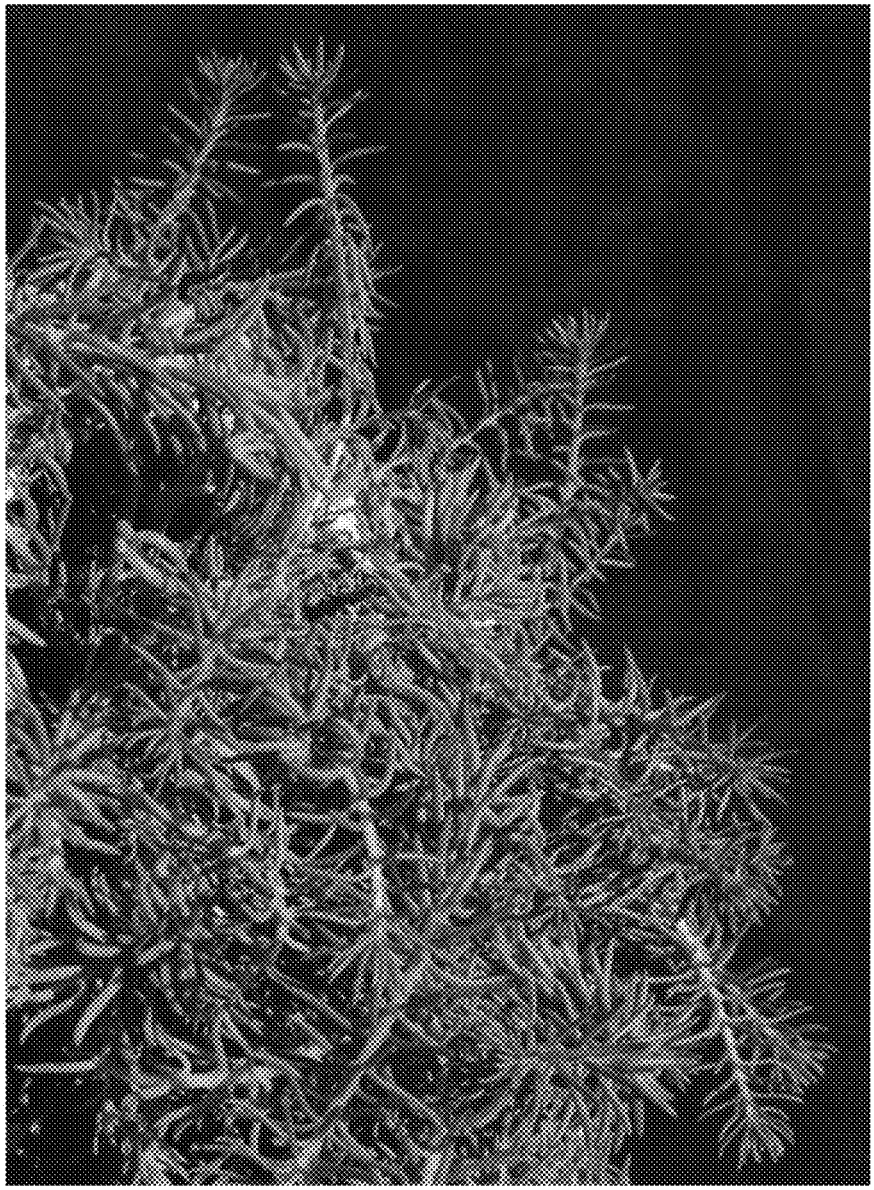

Botanical designation: *Sedum rupestre.*
Cultivar denomination: 'GOLD FORM'.

BACKGROUND OF THE INVENTION

The present invention relates to a new and distinct cultivar of *Sedum* plant, botanically known as *Sedum rupestre* and hereinafter referred to by the name 'Gold Form'.

The new *Sedum* plant is a naturally-occurring branch mutation of *Sedum rupestre* 'Angelina', not patented. The new *Sedum* plant was discovered and selected by the Inventor on a single plant within a population of plants of 'Angelina' in a controlled greenhouse environment in Cardington, Ohio in 2014.

Asexual reproduction of the new *Sedum* plant by terminal vegetative cuttings in a controlled greenhouse environment in Cardington, Ohio since 2014 has shown that the unique features of this new *Sedum* plant are stable and reproduced true to type in successive generations.

SUMMARY OF THE INVENTION

Plants of the new *Sedum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Gold Form'. These characteristics in combination distinguish 'Gold Form' as a new and distinct *Sedum* plant:

1. Compact, dense and bushy growth habit.
2. Initially upright to trailing to weeping and decumbent plant habit.
3. Freely basally and laterally branching habit.
4. Yellow green-colored leaves; color is stable year-round.
5. Good garden performance and winter hardiness.

Plants of the new *Sedum* differ from plants of the mutation parent, 'Angelina', primarily in the following characteristics:

1. Plants of the new *Sedum* are more compact than and not as sprawling as plants of 'Angelina'.
2. Plants of the new *Sedum* are less vigorous than plants of 'Angelina'.
3. Plants of the new *Sedum* are more freely branching than plants of 'Angelina'.
4. Leaves of plants of the new *Sedum* maintain their yellow green color year-round whereas leaves of plants of 'Angelina' become more yellow during the summer and orange red in color in the winter.
5. Plants of the new *Sedum* have not been observed to produce flowers whereas plants of 'Angelina' produce flowers during the summer.

Plants of the new *Sedum* can be compared to plants of *Sedum rupestre* 'Lemon Ball', not patented. Plants of the new *Sedum* and 'Lemon Ball' differ primarily in the following characteristics:

1. Plants of the new *Sedum* are more rounded than and not as mounding as plants of 'Lemon Ball'.
2. Leaves of plants of the new *Sedum* are more green in color than and not as yellow as leaves of plants of 'Lemon Ball'.

3. Plants of the new *Sedum* are more winter hardy than plants of 'Lemon Ball'.

BRIEF DESCRIPTION OF THE PHOTOGRAPHS

The accompanying colored photographs illustrate the overall appearance of the new *Sedum* plant showing the colors as true as it is reasonably possible to obtain in colored reproductions of this type. Colors in the photographs may differ slightly from the color values cited in the detailed botanical description which accurately describe the colors of the new *Sedum* plant.

The photograph on the first sheet comprises a side perspective view of a typical plant of 'Gold Form' grown in a container.

The photograph on the second sheet is a close-up view of a typical plant of 'Gold Form'.

DETAILED BOTANICAL DESCRIPTION

The aforementioned photographs and following observations, measurements and values describe plants grown during the summer in 2.5-quart containers in an outdoor nursery in Elburn, Ill. and under cultural practices typical of commercial *Sedum* production. During the production of the plants, day temperatures ranged from 13° C. to 27° C., night temperatures ranged from 7° C. to 18° C. and light levels ranged from 5,000 to 8,000 foot-candles. Plants were 20 weeks old when the photographs and description were taken. In the following description, color references are made to The Royal Horticultural Society Colour Chart, 2015 Edition, except where general terms of ordinary dictionary significance are used.

Botanical classification: *Sedum rupestre* 'Gold Form'.

Parentage: Naturally-occurring branch mutation of *Sedum rupestre* 'Angelina', not patented.

Propagation:

*Type*.—By terminal vegetative cuttings.

*Time to initiate roots, summer and winter*.—About seven to ten days at temperatures ranging from 18° C. to 21° C.

*Time to produce a rooted young plant, summer and winter*.—About 14 to 20 days at temperatures ranging from 18° C. to 21° C.

*Root description*.—Thin, fleshy; typically white in color, actual color of the roots dependent on substrate composition, water quality, fertilizer, substrate temperature and age of roots.

*Rooting habit*.—Moderately freely branching; medium density.

Plant description:

*Plant and growth habit*.—Herbaceous perennial; compact, dense and bushy growth habit; initially upright to trailing, weeping and decumbent habit; moderately vigorous growth habit; freely basally and laterally branching habit with numerous primary basal branches each with about two to four lateral branches developing per plant.

*Plant height*.—About 9 cm.

*Plant width* (*spread*).—About 32 cm.

*Lateral branches*.—Length: About 30 cm to 37 cm. Diameter: About 3 mm to 3.5 mm. Internode length: About 2 cm to 5 cm. Strength: Moderately strong, flexible. Texture and luster: Smooth, glabrous; slightly glossy. Color, developing and developed: Close to 144A.

Leaf description:

*Arrangement*.—Whorled, simple; sessile.

*Length*.—About 2.5 cm.

*Width*.—About 2 mm.

*Shape*.—Acicular.

*Apex*.—Acute.

*Base*.—Clasping.

*Margin*.—Entire.

*Texture and luster, upper and lower surfaces*.—Smooth, glabrous; succulent; slightly glossy.

*Venation pattern*.—Parallel.

*Color*.—Developing leaves, upper and lower surfaces: Close to 144A. Fully expanded leaves, upper and lower surfaces: Close to 144A to 144B; venation, close to 144A to 144B.

Flower description: To date, flower development has not been observed on plants of the new *Sedum*.

Pathogen & pest resistance: To date, plants of the new *Sedum* have not been noted to be resistant to pathogens and pests common to *Sedum* plants.

Garden performance: Plants of the new *Sedum* have been observed to have good garden performance and to tolerate rain, wind and temperatures ranging from −28° C. to 38° C.

It is claimed:

1. A new and distinct *Sedum* plant named 'Gold Form' as illustrated and described.

* * * * *